(12) United States Patent  (10) Patent No.: US 8,501,121 B1
Ulbrich et al.  (45) Date of Patent: Aug. 6, 2013

(54) TISSUE EMBEDDING APPARATUS, AND METHOD FOR OPERATING A TISSUE EMBEDDING APPARATUS

(71) Applicant: Leica Biosystems Nussloch GmbH, Nussloch (DE)

(72) Inventors: Hermann Ulbrich, Bad-Schonborn-Mingolsheim (DE); Karl-Heinz Westerhoff, Eppingen-Eisenz (DE); Stefan Künkel, Karlsruhe (DE)

(73) Assignee: Leica Biosystems Nusslock GmbH, Nussloch (DE)

( * ) Notice: Subject to any disclaimer, the term of this patent is extended or adjusted under 35 U.S.C. 154(b) by 0 days.

(21) Appl. No.: 13/853,854

(22) Filed: Mar. 29, 2013

Related U.S. Application Data

(63) Continuation of application No. 12/599,050, filed as application No. PCT/EP2008/054908 on Apr. 23, 2008, now Pat. No. 8,431,091.

(30) Foreign Application Priority Data

May 8, 2007 (DE) .......................... 10 2007 022 014

(51) Int. Cl.
*A61B 10/00* (2006.01)

(52) U.S. Cl.
USPC .............. 422/536; 422/50; 422/500; 422/501

(58) Field of Classification Search
USPC .................................... 422/50, 500–501, 536
See application file for complete search history.

(56) References Cited

U.S. PATENT DOCUMENTS

2004/0009098 A1\* 1/2004 Torre-Bueno .................. 422/63

\* cited by examiner

*Primary Examiner* — Jyoti Nagpaul
(74) *Attorney, Agent, or Firm* — Hodgson Russ LLP

(57) ABSTRACT

The present disclosure relates to a method for automatically embedding at least one tissue sample. A tissue embedding apparatus (1) can be provided having an input unit (2), an image acquisition unit (3), an embedding unit (4), at least one output unit (5, 6), and a control unit (7). A cassette (9) containing at least one tissue sample (8) can be transferred to the input unit (2) of the tissue embedding apparatus (1). At least one image of the tissue sample (8) and/or at least one image of the cassette (9) may be acquired using the image acquisition unit (3). The at least one image acquired of the tissue sample (8) and/or of the cassette (9) may be evaluated. Further processing the tissue sample (8) in the tissue embedding apparatus (1) can be performed as a function of the image evaluation.

5 Claims, 3 Drawing Sheets

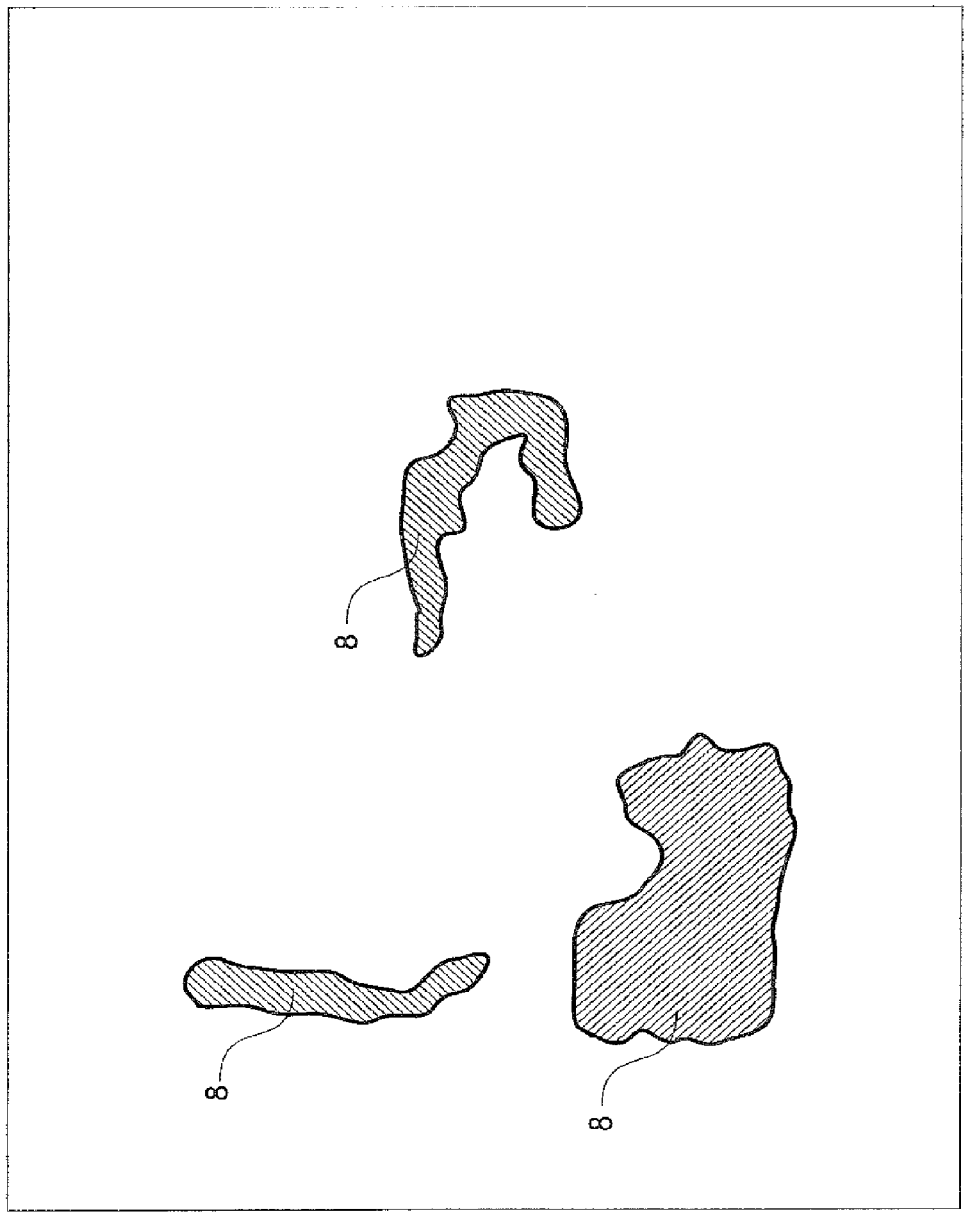

Figure 1:
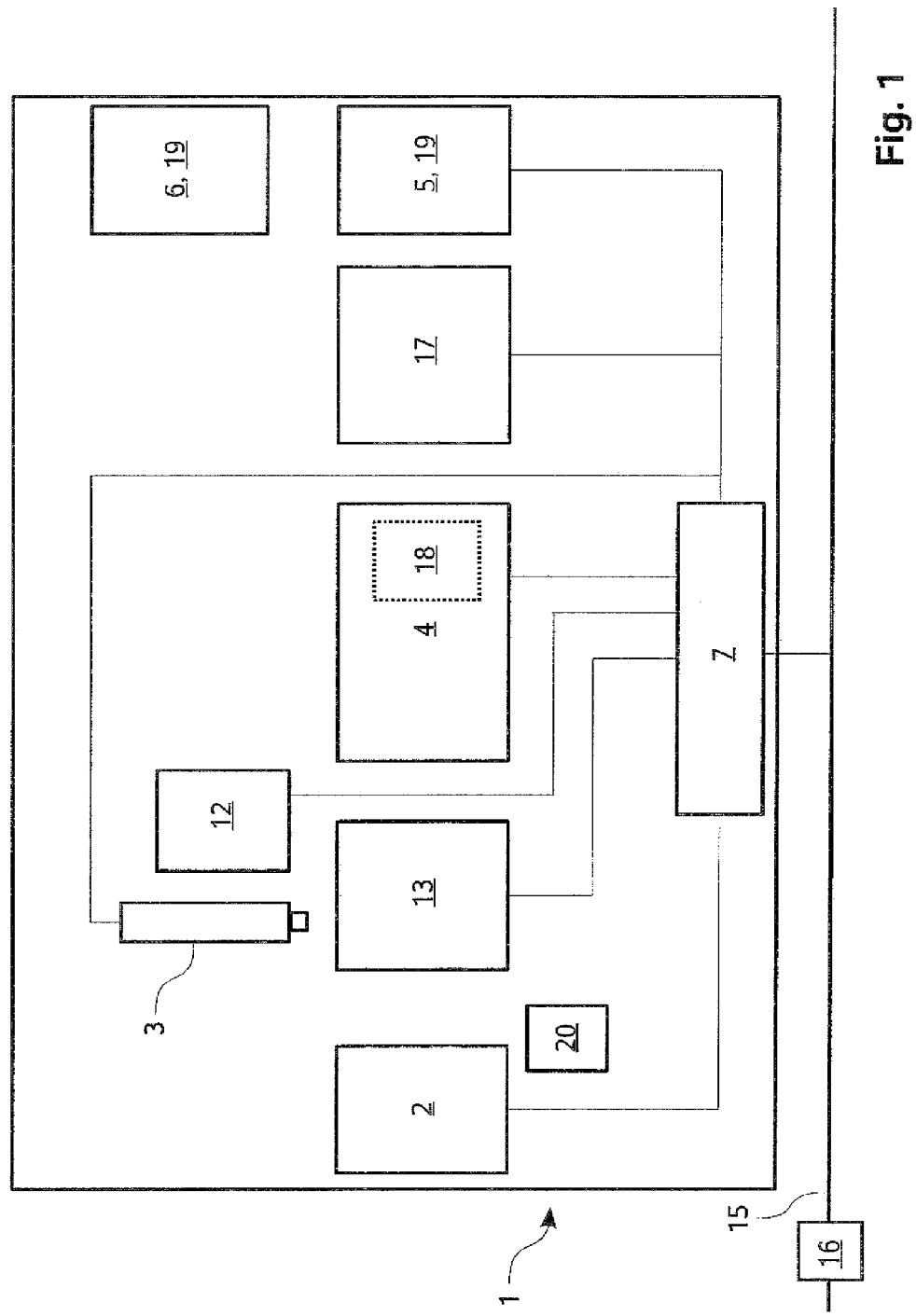

TISSUE EMBEDDING APPARATUS, AND METHOD FOR OPERATING A TISSUE EMBEDDING APPARATUS

FIELD OF THE INVENTION

The present invention relates to a tissue embedding apparatus for automatic embedding of at least one tissue sample. The tissue embedding apparatus encompasses an input unit, an image acquisition unit, an embedding unit, at least one output unit, and a control unit. A cassette containing at least one tissue sample is transferable to the input unit of the tissue embedding apparatus. By means of the embedding unit, the tissue sample is embeddable, preferably in automated fashion, in an embedding medium. The embedded tissue sample is outputtable with the at least one output unit or to a storage device. At least one image of the tissue sample is acquirable with the image acquisition unit. The present invention further relates to a method for operating a tissue embedding apparatus.

BACKGROUND OF THE INVENTION

Tissue embedding apparatuses of the kind recited above have been known from some time from the existing art. They are used for embedding tissue samples in an embedding medium such as, for example, paraffin or plastic. Reference is made, merely by way of example, to DE 102 23 304 A1, in which a tissue embedding apparatus is described. A tissue embedding apparatus of this kind is usually operated manually by a technician, for example an MTA (medical technical assistant). An embedding unit usually comprises a pouring station for melted embedding medium or paraffin. The purpose is to immobilize or embed one or more tissue samples in the embedding medium in such a way that the block containing the tissue sample can be clamped in a microtome, so that thin sections thereof can be produced for microscopic investigation. A disadvantage with a manually actuable tissue embedding apparatus is a possible risk of confusion of the tissue samples during the processing operation in the tissue embedding apparatus. In addition, the quality of the embedded tissue samples varies as the personnel changes.

Automated tissue embedding apparatuses are known from the existing art. Reference is made, merely by way of example, to WO 2004/029584 A1. Before the tissue samples are embedded using this tissue embedding apparatus, the tissue samples must be wrapped in a fine net. The tissue sample is automatically embedded in the embedding medium together with the net. This also means, however, that the net must be sectioned in the context of the sectioning operation with the microtome. This causes a greater degree of wear on the microtome blades, which results in increased consumption of microtome blades. In addition, it is necessary to use cassettes specially provided for the tissue embedding apparatus, which can be associated with additional cost.

SUMMARY OF THE INVENTION

The underlying object of the present invention is therefore to describe and further develop a tissue embedding apparatus of the kind cited initially, and a method for operating a tissue embedding apparatus, that solve the problems presented. In particular, it is intended to be possible to affect tissue embedding even with the use of different cassettes.

The tissue embedding apparatus according to the present invention of the kind cited initially achieves the aforesaid object by way of the features described herein. In accordance therewith, a tissue embedding apparatus of this kind is characterized in that the image acquired of the tissue sample is evaluatable, and the further processing of the tissue sample in the tissue embedding apparatus is definable as a function of the image evaluation. The further processing of the tissue sample encompasses, in particular, the embedding of the tissue sample.

What has been recognized according to the present invention is firstly that it is not necessary to use special cassettes for automatic embedding using a tissue embedding apparatus, since there are only a limited number of different target orientations of the tissue samples for the embedded state. The number of possible initial orientations of the tissue samples in a cassette is also limited, so that for transfer of an initial orientation of the tissue sample to a target orientation of the tissue sample, only a limited number of manipulation steps, which can be standardized, need to be provided. This can be achieved in almost all cases with the use of image evaluation of the acquired images of a tissue sample, by the fact that a tissue sample is manipulated, and thereby arranged, in such a way that embedding in an embedding medium for high-quality further processing, for example for microtoming, is possible. In the few exceptional cases in which this does not seem to be possible, provision could be made for exceptional treatment of the respective tissue samples, for example by picking out and conventionally manually embedding the few individual tissue samples. Because such exceptional treatments are only seldom necessary, this is acceptable, since faster and more uniform embedding of the tissue samples can be achieved overall with the tissue embedding apparatus according to the present invention.

Provision could thus be made that a tissue sample is removed from the cassette and automatically transferred into a casting mold. If only one tissue sample is present in the cassette, it is arranged centeredly and in planar fashion on the bottom of the casting mold. If multiple tissue samples (usually 2 to 5) are present in the cassette, they are distributed with an almost uniform spacing next to one another, in planar fashion on the bottom of the casting mold. The arrangement of multiple tissue samples on the bottom of the casting mold is then accomplished, by preference, in a manner comparable to the arrangement of the spots on a die.

Evaluation of the acquired image could be carried out by means of digital image processing methods. This is accomplished, preferably, without substantial time delay with respect to image acquisition. A computer or control computer could execute corresponding image acquisition programs and/or image evaluation programs both for image acquisition and for image evaluation, the computer being associated with the tissue embedding apparatus, or the control unit of the tissue embedding apparatus also handling that task.

In the context of digital image processing, for example, the image of a tissue sample could be segmented using a segmenting algorithm in order to separate the image of the tissue sample from the background or from the remainder of the image. A threshold algorithm, which does not consider all the grayscale values and/or color values of the image elements (pixels) of the acquired image that lie below or above a definable threshold, could be used here. In addition, all the grayscale values and/or color values of the image elements of the acquired image that lie inside or outside a definable threshold region could not be considered. An acquired image can, in principle, be an image acquired in reflected-light or transmitted-light mode. The grayscale values and/or color values of the acquired image can correspondingly encompass reflection values or extinction values of a tissue sample.

Additionally or alternatively, an algorithm could be used that takes into account the theoretically possible shapes of the tissue samples and, so to speak, carries out a comparison of the acquired shape or outer contours of the tissue sample with stored usual shapes of tissue samples. In comparable fashion, it is possible for the image of a tissue sample, or the image portion representing the tissue sample, to be categorizable and/or classifiable on the basis of a pattern comparison, in particular on the basis of the nature of the tissue sample surfaces.

The purpose of evaluating the acquired image is, in particular, to ascertain the type and/or position and/or shape of the tissue sample. It is further intended to be possible to ascertain the number of tissue samples on the basis of the image of the tissue sample or samples, and/or on the basis of the image portion representing the tissue sample. These results can be used in the context of further processing of the respective tissue sample in the tissue embedding apparatus, for example, in order to align and/or position a tissue sample for preparation of the embedding operation. It may also be necessary in this context to acquire and evaluate further images of the tissue sample in order to achieve the most optimal embedding result.

An image-producing imaging device, for example a confocal scanner, could be used in principle as an image acquisition unit for acquiring an image of the tissue sample. A confocal scanner has the fundamental advantage that because of the confocal imaging principle, a tissue sample is imaged within a relatively small depth-of-focus region, so that it is possible to ascertain the dimensions of the tissue sample in a direction perpendicular to the support surface of the tissue sample (for example, in the cassette or the casting mold), i.e. its thickness. With this information it is correspondingly possible to calculate how much embedding medium is necessary for optimum embedding of the particular sample. Alternatively or additionally, the image acquisition unit comprises a grayscale camera or a color camera, in particular a CCD camera. This is preferably a digital camera, so that immediately after image acquisition a digital image, or an image sequence of digital images, is available that can be evaluated or analyzed using digital image processing methods. The camera could comprise a calibrated autofocus system with which the surface of the tissue sample facing the camera can be focused and thus imaged sharply. Conclusions can thereby also be drawn indirectly as to the dimensions of the tissue sample in a direction perpendicular to the support surface of the tissue sample.

The grayscale-value information and/or color-value information of the acquired image could be usable for image evaluation. It is conceivable, for example, that for certain tissue samples, a pattern evaluation of acquired images on the basis of grayscale-value information arrives at a result faster and/or more reliably than can be the case with another procedure. With other types of tissue samples, this might be the case when the color information is taken into consideration.

If a tissue sample turns out not be classifiable and/or evaluatable, in a preferred embodiment provision could be made that a separate treatment is provided for that tissue sample. A tissue sample of this kind could be deliverable for exceptional treatment in the tissue embedding apparatus, and/or said tissue sample could be transferred to a further output unit of the tissue embedding apparatus in order to pick out such a tissue sample and deliver it, for example, for manual processing or embedding.

In accordance with a particularly preferred embodiment, the tissue embedding apparatus comprises a manipulating unit. Provision is made that the manipulating unit, inter alia, transfers a tissue sample into a definable position, alignment and/or location, in particular according to a reference pattern. The manipulation could be provided on a tissue sample that is present in a cassette or in a casting mold. Provision could be made, in particular, that the tissue sample is transferred, with the aid of the manipulating unit, out of the cassette into a casting mold. In addition, the tissue sample could be aligned or positioned with the manipulating unit in the casting mold according to a definable pattern, in preparation for the sample's embedding operation.

The manipulating unit could comprise at least one means for manipulating the tissue sample. Concretely, the at least one means comprises a gripping arm and/or an air nozzle and/or an actuator for shaking and/or vibrating the cassette or the casting mold. The cassette, a casting mold, or the tissue sample itself could be gripped by a gripping arm. The gripping arm would correspondingly need to be suitably embodied, and the gripping arm should not damage the sample when grasping. An air nozzle can be provided for controlled manipulation of a tissue sample by the fact that, for the example, the tissue sample is impinged upon or blown onto, preferably locally, with a definable air flow in a definable direction.

Especially when the manipulating unit is used to orient the tissue sample immediately before the embedding operation, it is useful to arrange the image acquisition unit and the manipulating unit in physically adjacent or physically overlapping fashion. For example, before, during, and/or after the manipulation of the tissue sample, a respective image or respective image sequence can be acquired in order, for example, to check the result of the sample manipulation and to execute further manipulation steps if applicable. A predefined tissue sample arrangement and/or tissue sample alignment can be achieved in this fashion in an iterative procedure.

If the tissue sample is immobilized on the cassette or on another tissue sample, or is adhering thereto, because of a preceding processing step, for example by means of a tissue infiltration apparatus, provision could be made that the tissue sample that is in an unheated state is detachable from the cassette by heat input. A heat source, for example in the form of a microwave unit or a thermal radiator, could be provided in the tissue embedding apparatus for this purpose.

Embedding of the tissue sample with the embedding medium is usually accomplished by transferring the tissue sample into a casting mold and introducing the liquid embedding medium into the casting mold. In a preferred embodiment, this procedure is also provided for in the context of the tissue embedding apparatus according to the present invention. The tissue sample is correspondingly removed from the cassette and placed and/or immobilized in a casting mold. This casting mold is preferably temperature-controlled. It is useful in this context firstly to bring the casting mold to a temperature that is above the melting point of the wax with which a tissue sample might be equipped. During and/or after the embedding operation with the liquid embedding medium, it would be useful to bring the casting mold to a lower temperature in order to accelerate the hardening process of the liquid embedding medium. Embedding of the tissue sample takes place in the casting mold. The tissue sample is preferably placed and/or immobilized in the casting mold by the manipulating unit. Transfer of the tissue sample from the cassette into the casting mold could correspondingly be accomplished with the manipulating unit. It is also conceivable to tip the tissue samples that are present in the cassette out over the casting mold, if there is assurance that the tissue samples are not adhering to the cassette or immobilized thereon. Lastly, it is possible for the cassette to be embodied in such a way that at least a part of such a cassette takes on the function of the casting mold. In this case, transfer of the tissue samples from the cassette into a casting mold (for example, using the manipulating unit) would be superfluous.

As soon as the tissue sample is prepared for the embedding operation, the tissue sample is immobilized with the embedding medium. Paraffin or plastic is usual as an embedding medium. The embedding medium is added in a liquid aggregate state to the tissue sample. As soon as this has occurred, the tissue sample with the embedding medium will need to be cooled so that the liquid embedding medium can transition into a solid aggregate state. For this, the tissue sample plus embedding medium (in the casting mold) could be brought into contact with a cooling unit, for example a Peltier element, or could be transferred into a cooling area or cooling chamber provided therefor.

In accordance with a very particularly preferred embodiment, the tissue embedding apparatus is embodied in such a way that different types of cassettes are transferable to the tissue embedding apparatus and processable by the tissue embedding apparatus. In other words, in accordance with this exemplifying embodiment it is possible to transfer cassettes of different configurations, or from different manufacturers, to the tissue embedding apparatus. These could be ascertained on the basis of an identifying means provided on the cassette, as a result of which the further processing of the respective cassette, which is influenced by the configuration of the respective cassette, is known to the tissue embedding apparatus. Alternatively or additionally, an image of the cassette transferred to the tissue embedding apparatus could be acquired using the image acquisition unit. A conclusion could then be drawn as to the configuration of the cassette on the basis of the image of the cassette, for example by pattern comparison. By this means as well, the requisite further treatment of the respective cassette can be ascertained and carried out, for example, by the manipulating unit.

The cassette usually comprises a removable cover. Provision could accordingly be made that the cover of the cassette is removed with a manipulator. The manipulator could comprise a tool or a gripping arm specially provided therefor, which could be associated with the input unit. It would also be possible for the manipulator to represent part of the manipulating unit, with which unit the tissue sample can also be manipulated.

In accordance with a preferred embodiment, a cassette comprises an identification means. With the identification means, an identification of the cassette is possible. It is thereby possible also to draw conclusions as to the tissue sample or samples contained in the cassette, if it is possible to access reference data, for example from a patient database. The identification means could be a barcode and/or a machine-readable imprint and/or a transponder or a radio-frequency identification (RFID) tag.

Provision could then be made that, on the basis of the identification means, the present location or position of a cassette or a tissue sample within the tissue embedding apparatus is ascertainable. The remaining treatment time of a cassette or a tissue sample could also be ascertainable on the basis of the identification means. This feature can be helpful if a tissue sample or cassette needs to be accessed earlier than expected, and in this case the tissue sample can be processed manually.

Additionally or alternatively, provision could be made that on the basis of the data contained or encoded in an identification means of the cassette, the processing sequence of the cassettes or tissue samples received by the input unit is definable. In some circumstances, the data could contain information as to the priority with which a tissue sample contained in the cassette is to be processed. Such information could thus directly have an influence on the sequence of processing of the cassettes transferred to the tissue embedding apparatus.

In accordance with a preferred embodiment, the tissue embedding apparatus is incorporated into a laboratory control system. Further preparation units could also be controlled with a laboratory control system of this kind, for example a tissue infiltration apparatus or an automatic stainer, so that ideally, almost completely automated sample preparation is possible. Such incorporation of the tissue embedding apparatus or its control device could be implemented by linkage to a control computer for the laboratory control system via a network, and/or to a database system.

It might be useful in this connection for the processing sequence of the cassettes or tissue samples received by the input unit to be definable and/or modifiable, in more or less remotely controlled fashion, by the laboratory control system. This can be necessary when the processing sequence of individual tissue samples by means of the other preparation units and/or by means of the tissue embedding apparatus is to be modified.

Energy is preferably impingeable onto a tissue sample, in particular for a definable duration. The energy is, in particular, thermal energy or electromagnetic waves, for example microwaves and/or ultrasonic waves. This can be helpful or necessary when a tissue sample is adhering to a cassette or when multiple tissue samples are adhering to one another.

The actual embedding operation with the tissue embedding apparatus could in principle be accomplished semi-automatically. In this case the tissue sample or samples could be positioned or aligned in the casting mold by the manipulating unit. An image of the tissue sample(s) could then be made available to an operator on an output unit (for example, a monitor). If the position and/or alignment of the tissue sample in the casting mold is acceptable, the embedding operation could be initiated upon a corresponding input of the operator, said embedding operation ultimately proceeding entirely automatically. In accordance with a preferred embodiment, however, provision is made that the embedding operation proceeds automatically, and/or that the embedding medium is automatically poured in, specifically with no need for a previous operator input.

If the tissue sample is transferred out of the cassette into a casting mold and the embedding operation of the tissue sample occurs in the casting mold, in accordance with a preferred embodiment provision could be made that at least a part of the cassette is usable as a stabilization element and/or as a clamping element upon microtoming of the tissue sample embedded in the embedding medium. In this context, for example, this could be the part of the cassette that comprises an identification means onto which the not-yet-completely hardened embedding medium is applied. After hardening of the embedding medium, the consequently hardened block of the embedding medium, having the tissue sample and the part of the cassette that is now also fixedly joined to the hardened embedding medium, could be removed from the casting mold, and only the block with the cassette part could be further processed. The casting mold could be reused, optionally after cleaning.

As already set forth in the previous portion, provision could be made that after the embedding operation, the tissue sample embedded in the embedding medium is cooled in order to solidify the initially liquid embedding medium. Provided therefor in a preferred embodiment is a cooling unit, made available for this purpose, at or in which the tissue sample embedded in the embedding medium can be cooled.

In accordance with a preferred embodiment, the tissue embedding apparatus could comprise a post-processing unit. An embedded tissue sample is post-treatable with the post-processing unit. Post-treatment of the embedded tissue sample could encompass, in particular, the removal of superfluous residues of the embedding medium (deburring). Manipulators or corresponding tools could be provided for this.

Also in preferred fashion, the tissue embedding apparatus comprises a storage unit. At least one embedded tissue sample is storable at the storage unit. Storage of the embedded tissue samples in the storage unit could occur at a definable temperature. The definable temperature could be in a range from −10 to 20 degrees C.

The object recited initially is achieved by the method for automatically embedding at least one tissue sample described herein. The tissue embedding apparatus encompasses an input unit, an image acquisition unit, an embedding unit, at least one output unit, and a control unit. A cassette containing at least one tissue sample is transferred to the input unit of the tissue embedding apparatus. By means of the embedding unit, the tissue sample is embedded (in particular, in automated fashion) in an embedding medium. The embedded tissue sample is outputted with the at least one output unit. At least one image of the tissue sample is acquired with the image acquisition unit. The method according to the present invention is characterized in that the image acquired of the tissue sample is evaluated, and the further processing of the tissue sample in the tissue embedding apparatus is defined as a function of the image evaluation.

The method according to the present invention serves in particular for the operation of a tissue embedding apparatus as described herein, so that reference is made to the preceding portion of the description in order to avoid repetition with regard to apparatus features relevant thereto. The method steps necessary for operation of the tissue embedding apparatus are apparent in this context to a skilled artisan active in the present field having a knowledge of the disclosure content of the preceding portion of the description.

BRIEF DESCRIPTION OF THE DRAWING VIEWS

Figure 2:
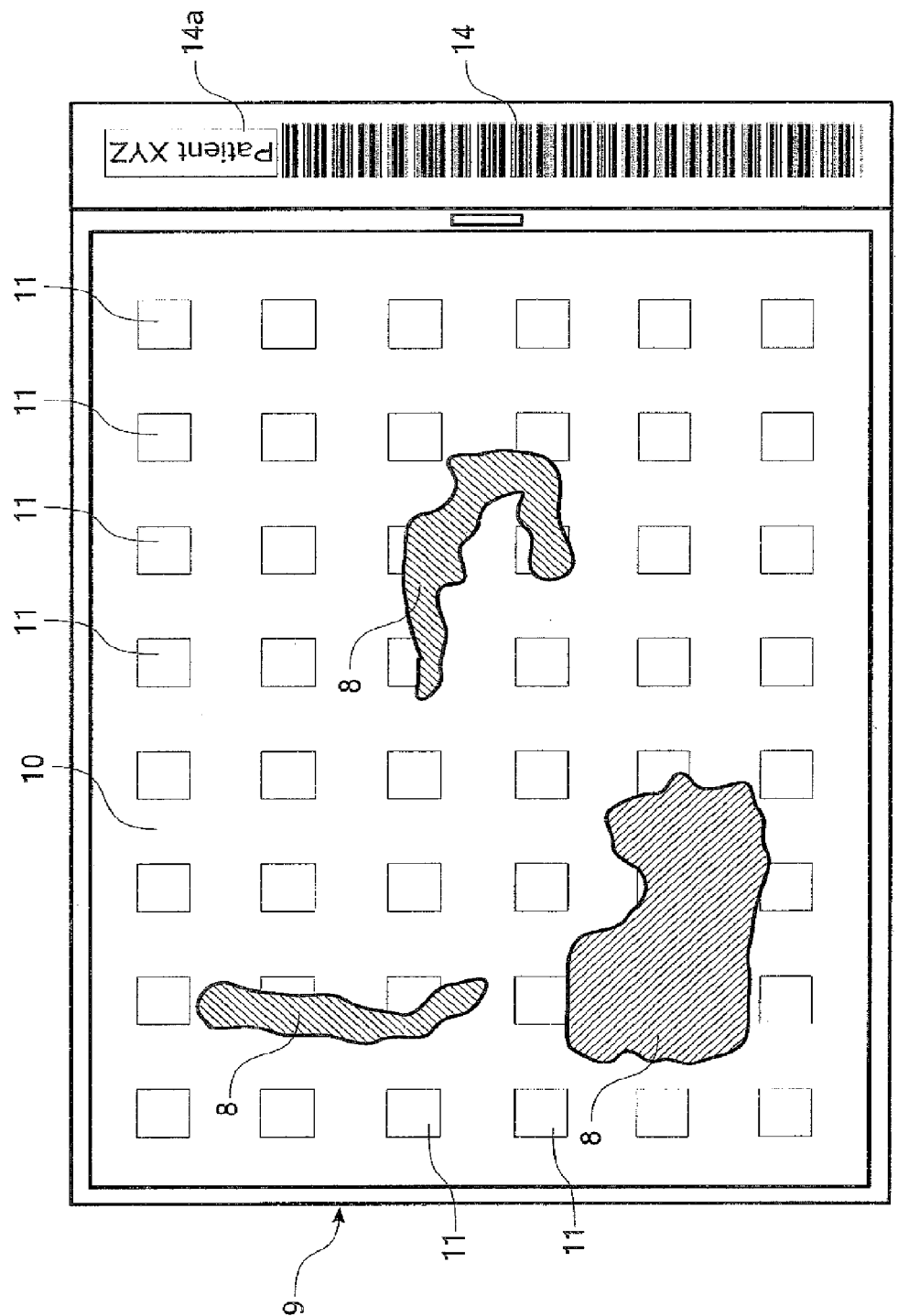

There are various ways of advantageously embodying and further developing the teaching of the present invention. The reader is referred, for that purpose, to the explanation below of the preferred exemplifying embodiments of the invention with reference to the drawings. In conjunction with the explanation of the preferred exemplifying embodiments of the invention with reference to the drawings, an explanation will also be given of generally preferred embodiments and further developments of the teaching. In the drawings:

FIG. 1 schematically depicts an exemplifying embodiment of a tissue embedding apparatus according to the present invention;

FIG. 2 schematically depicts an image of three tissue samples that has been acquired, in an open cassette, by the image acquisition unit; and FIG. 3 schematically depicts the image of FIG. 2 in which the imaged tissue samples are separated from the image background by means of a segmentation algorithm.

DETAILED DESCRIPTION OF THE INVENTION

Identical or similar components are identified in the Figures using the same reference characters. FIG. 1 shows a tissue embedding apparatus 1. Tissue embedding apparatus 1 encompasses an input unit 2, an image acquisition unit 3, an embedding unit 4, at least one output unit 5, 6, and a control unit 7. A cassette (not shown in FIG. 1) containing at least one tissue sample is transferable to input unit 2 of tissue embedding apparatus 1. Transport of cassettes 9 in tissue embedding apparatus 1 is accomplished by means of a transport system (not shown). The tissue sample can be embedded in an embedding medium by means of embedding unit 4. The embedded tissue sample can be outputted with the at least one output unit 5. At least one image of the tissue sample can be acquired with image acquisition unit 3. One such image is shown schematically in FIG. 2. Three tissue samples 8 are shown, in this context, in a cassette 9. Cassette bottom 10 of cassette 9 is shown, which bottom comprises openings or cutouts 11 through which liquids can pass.

In a manner according to the present invention, the image acquired of tissue sample 8 can be evaluated, and the further processing of tissue sample 8 in tissue embedding apparatus 1 can be defined as a function of the image evaluation.

In this exemplifying embodiment, evaluation of the acquired image is carried out by means of digital image processing methods. In this context, the image of a tissue sample is segmented, using a segmentation algorithm, in order to ascertain the external shape of the tissue sample. The image shown in FIG. 2 is shown in FIG. 3 in a segmented state. In addition, the image of tissue sample, or the image portion representing the tissue sample, is categorized and/or classified on the basis of a pattern comparison. The positions and shapes of the tissue samples, and their number, can thereby be ascertained. In the image shown in FIG. 3, the three tissue samples 8 have been automatically categorized as two punched-out pieces and one larger tissue piece. Images comparable to those shown in FIGS. 2 and 3 are acquired, processed and evaluated during and after transfer of a tissue sample 8 out of cassette 9 into a casting mold, and before and during manipulation of a tissue sample 8 in cassette 9 or in the casting mold, and also before and during the embedding operation.

Image acquisition unit 3 is a black-and-white CCD camera with which grayscale images can be acquired. The grayscale-value information of the acquired image is utilized for image evaluation.

If one of the tissue samples cannot be classified or analyzed, it is delivered for separate treatment. Concretely, such tissue samples 8 in cassettes 9 are delivered, without further treatment, to output unit 6, where they can be removed by a technician and processed and embedded using a conventional manual tissue embedding apparatus.

Tissue embedding apparatus 1 comprises a manipulating unit 12 with which a tissue sample 8 is transferable into a definable position, alignment, and/or location, in particular according to a reference pattern. Manipulating unit 12 is shown only schematically in FIG. 1. It comprises at least one means for manipulating a tissue sample 8. A means of this kind encompasses a gripping arm, an air nozzle, and/or an actuator for shaking or vibrating cassette 9 or the casting mold. Image acquisition unit 3 and manipulating unit 12 are physically adjacent to one another. Both image acquisition unit 3 and manipulating unit 12 act on processing unit 13, where images of cassettes 9 or tissue samples 8 are acquired using image acquisition unit 3, and where tissue samples 8 are manipulated by manipulating unit 12. Processing unit 13 thus has a temperature-controllable region in which a casting mold (not shown) can be arranged. Tissue sample 8 is transferred by manipulating unit 12 into a casting mold; this could also be performed by gripping the cassette and tipping out the cassette over the casting mold.

Tissue samples 8, arranged in the casting mold and previously immobilized, are transferred to embedding unit 4. There they are embedded with liquid embedding medium, specifically with paraffin or with a plastic.

The cassettes usually comprise a removable cover (not shown). A cover of this kind is removed with a manipulator (not shown) of manipulating unit 12, so that cassette 9 having tissue samples 8 is comparable in appearance to the image shown in FIG. 2 and is accessible to manipulating unit 12.

Cassette 9 comprises an identification means 14, 14a with which an identification of cassette 9 is possible. Conclusions can be drawn therefrom as to the tissue samples 8 contained in cassette 9, if this was previously entered into and stored in a database system in corresponding fashion. Identification means 14 comprises a machine-readable imprint that is embodied in the form of a barcode. Identification means 14a comprises a readable imprint from which the patient's name can be read off directly. Identification means 14, 14a can be read with reading unit 20. Reading unit 20 encompasses a barcode scanner and a character recognition (OCR) unit. The location of a cassette 9 or a tissue sample 8 within tissue embedding apparatus 1 can be ascertained on the basis of identification means 14.

Tissue embedding apparatus 1 is incorporated via control unit 7 into a laboratory control system (not shown) via a network 15. Control computer 16 of the laboratory control system applies control to tissue embedding apparatus 1 and to other, further laboratory units not shown in FIG. 1. Control computer 16 comprises a database system or has access thereto. Data and information about the patients and the tissue samples 8 and cassettes 9 prepared from them are stored in the database system.

The embedding operation proceeds entirely automatically in embedding unit 4. The embedding medium is added automatically. A further image acquisition unit could be provided, with which the embedding operation in embedding unit 4 can be monitored.

The part of cassette 9 shown in FIG. 2 serves as a stabilization element and a clamping element upon microtoming of the embedded tissue sample 8. Firstly the empty cassette 9 is applied onto the block of not-yet-solidified embedding medium (in which the tissue sample is located). As a result, the block having identification means 14, 14a in cassette 9 continues to be identifiable even outside the tissue embedding apparatus.

An embedded tissue sample 8 can be post-treated with post-processing unit 17. Excess residues of the embedding medium are removed, in particular, in this context.

Embedding unit 4 comprises a cooling unit 18 with which the embedding medium can be cooled off immediately after the embedding operation. Cooling unit 18 is indicated merely schematically with dashed lines, and comprises a Peltier element with which a casting mold can be brought into contact.

The two output units 5, 6 also have the functions of a storage unit 19 in which the embedded tissue samples are stored. A definable temperature, which is equal substantially to 5 degrees C., exists in storage unit 19.

In conclusion, be it noted very particularly that the exemplifying embodiments discussed above serve merely to describe the teaching claimed, but do not limit it to the exemplifying embodiments.

What is claimed is:

1. A method for automatically embedding at least one tissue sample comprising the steps of:
   providing a tissue embedding apparatus (1) comprising an input unit (2), an image acquisition unit (3), an embedding unit (4), at least one output unit (5, 6), and a control unit (7),
   transferring a cassette (9) containing at least one tissue sample (8) to the input unit (2) of the tissue embedding apparatus (1),
   acquiring at least one image of the tissue sample (8) and/or at least one image of the cassette (9) using the image acquisition unit (3),
   evaluating the at least one image acquired of the tissue sample (8) and/or of the cassette (9), and
   further processing the tissue sample (8) in the tissue embedding apparatus (1) as a function of the image evaluation.

2. The method according to claim 1, wherein the further processing includes aligning and/or positioning the tissue sample in preparation for an embedding operation in the embedding unit.

3. The method according to claim 1, further comprising evaluating the at least one image of the cassette (9) and further treatment of the cassette on the basis of the image evaluation.

4. The method according to claim 3, wherein the evaluating step is ascertained on the basis of an identifier provided on the respective cassette (9).

5. The method according to claim 4, wherein the identifier is one or more of the following: a bar code, a machine-readable imprint, form of the cassette (9), color of the cassette (9), and a transponder or a radio-frequency identification (RFID) tag.

* * * * *

UNITED STATES PATENT AND TRADEMARK OFFICE
CERTIFICATE OF CORRECTION

| | | |
|---|---|---|
| PATENT NO. | : 8,501,121 B1 | Page 1 of 1 |
| APPLICATION NO. | : 13/853854 | |
| DATED | : August 6, 2013 | |
| INVENTOR(S) | : Ulbrich et al. | |

It is certified that error appears in the above-identified patent and that said Letters Patent is hereby corrected as shown below:

Title page, item (73), the Assignee should read:

--Leica Biosystems Nussloch GmbH,
          Nussloch (DE)--

Signed and Sealed this
Seventeenth Day of September, 2013

Teresa Stanek Rea
*Deputy Director of the United States Patent and Trademark Office*